United States Patent [19]
Gan et al.

[11] Patent Number: 5,523,316
[45] Date of Patent: Jun. 4, 1996

[54] INTRAOCULAR IRRIGATING SOLUTION CONTAINING AGENT FOR CONTROLLING IOP

[75] Inventors: Owen Gan, Arlington; Rajni Jani; Ole J. Lorenzetti, both of Fort Worth, all of Tex.

[73] Assignee: Alcon Laboratories, Inc., Fort Worth, Tex.

[21] Appl. No.: 264,812

[22] Filed: Jun. 23, 1994

[51] Int. Cl.$^6$ ............................................. A61K 31/415
[52] U.S. Cl. ........................ 514/392; 514/912; 514/255
[58] Field of Search ................................. 514/392, 255, 514/912

[56] References Cited

U.S. PATENT DOCUMENTS

| | | | |
|---|---|---|---|
| 3,468,887 | 9/1969 | Stahle et al. | 260/253 |
| 4,461,904 | 7/1984 | York, Jr. | 548/315 |
| 4,515,800 | 5/1985 | Cavero et al. | 514/392 |
| 4,517,199 | 5/1985 | York, Jr. | 514/392 |
| 4,550,022 | 10/1985 | Garabedian et al. | 424/127 |
| 4,587,257 | 5/1986 | DeSantis | 514/392 |
| 4,975,419 | 12/1990 | Newton et al. | 514/6 |
| 5,212,196 | 5/1993 | House et al. | 514/392 |
| 5,215,991 | 6/1993 | Burke | 514/255 |

FOREIGN PATENT DOCUMENTS

| | | |
|---|---|---|
| 0076658 | 4/1983 | European Pat. Off. . |
| 0358369 | 3/1990 | European Pat. Off. . |

OTHER PUBLICATIONS

Evans, Dale B., et al., "β–Adrenergic Receptor Blockers as Therapeutic Agents", *Annual Reports in Medicinal Chemistry*, vol. 14, pp. 81–90 1979.

Machin, Peter J., et al., "β$_1$–Selective Adrenoceptor Antagonists. 2. 4–Ether–Linked Phenoxypropanolamines", *Journal of Medicinal Chemistry*, vol. 26, No. 11, pp. 1570–1576 (Nov. 1983).

Machin, Peter J., et al., "β$_1$–Selective Adrenoceptor Antagonists. 3. 4–Azolyl–Linked Phenoxypropanolamines", *Journal of Medicinal Chemistry*, vol. 27, No. 4, pp. 503–509 (Apr. 1984).

Pitha, Josef, et al., "β–Adrenergic Antagonists with Multiple Pharmacophores: Persistent Blockade of Receptors", *Journal of Medicinal Chemistry*, vol. 26, No. 1, pp. 7–11 (Jan. 1983).

Kierstead, R. W., et al., "β$_1$–Selective Adrenoceptor Antagonists. 1. Synthesis and β–Adrenergic Blocking Activity of a Series of Binary (Aryloxy) propanolamines", *Journal of Medicinal Chemistry*, vol. 26, No. 11, pp. 1561–1567 (Nov. 1983).

Erhardt, Paul W., et al., "Ultra–Short–Acting β–Adrenergic Receptor Blocking Agents. 3. Ethylenediamine Derivatives of (Aryloxy) propanolamines Having Esters on the Aryl Function", *Journal of Medicinal Chemistry*, vol. 26, No. 8, pp. 1109–1112 (Aug. 1983).

Baldwin, John J., et al., "β$_1$–Selective Adrenoceptor Antagonists: Examples of the 2–[4–[3–(Substituted–amino)–2–hydroxypropoxy[phenyl[imidazole Class", *Journal of Medicinal Chemistry*, vol. 26, No. 7, pp. 950–957 (Jul. 1983).

McClure, David E., et al., "Antihypertensive β–Adrenergic Blocking Agents: N–Aralkyl Analogues of 2–[3–(tert–Butylamino)–2–hydroxypropoxy]–3–cyanopyridine$^1$", *Journal of Medicinal Chemistry*, vol. 26, No. 5, pp. 649–657 (May 1983).

Large, M. S., et al., "β–Adrenergic Blocking Agents. 23. 1–[(Substituted–amido)phenoxy]–3–[[(substituted–amido)alkyl]amino]propan–2–ols", *Journal of Medicinal Chemistry*, vol. 26, No. 3, pp. 352–357 (Mar. 1983).

Rouot, Bruno, et al., "Clonidine and Related Analogues. Quantitative Correlations" *Journal of Medicinal Chemistry*, vol. 19, pp. 1049–1054 (1976).

Timmermans, et al., "Structure–Activity Relationships in Clonidine–Like Imidazolidines and Related Compounds", published in 1980 by Gustav Fischer Verlag, of Stuttgart and New York, pp. 1–97.

*Primary Examiner*—Paul J. Killos
*Attorney, Agent, or Firm*—Sally Yeager; Gregg C. Brown

[57] ABSTRACT

Improved ophthalmic irrigating solutions are described. The solutions include one or more drugs for controlling intraocular pressure, an antioxidant/free radical scavenger, electrolytes, a cellular energy source, bicarbonate, and a buffer. Methods of using the solutions in connection with ophthalmic surgical procedures are also described.

40 Claims, No Drawings

INTRAOCULAR IRRIGATING SOLUTION CONTAINING AGENT FOR CONTROLLING IOP

BACKGROUND OF INVENTION

1. Field of the Invention

The present invention relates to the field of ophthalmology. More particularly, the invention relates to an improved intraocular irrigating solution for controlling intraocular pressure ("IOP") during intraocular surgical procedures while maintaining the integrity, stability, and function of ocular tissues.

2. Discussion of Related Art

The growth of new surgical techniques and associated products over the past decade has been quite remarkable. For example, cataract surgery, which is a very delicate operation involving replacement of the natural crystallin lens of the human eye with an artificial lens, was previously considered to be a major surgical procedure requiring hospitalization of the patient and a significant recovery period, but today this procedure is routinely performed on an out-patient basis and enables vision to be restored almost immediately. Similar advancements have been achieved in other areas of ophthalmic surgery. These remarkable advancements are attributable to various factors, including improved equipment for performing the surgeries, improved surgical techniques developed by innovative surgeons, and improved pharmaceutical products which facilitate successful surgery by minimizing the risks of damaging sensitive, irreplaceable ocular tissue during surgery. The present invention is directed to a further improvement in one such pharmaceutical product, a solution for irrigating ocular tissue during intraocular surgery. Such solutions are discussed in U.S. Pat. No. 4,550,022; the entire contents of that patent are hereby incorporated in the present specification by reference. The importance of such solutions to ophthalmic medicine is explained in the '022 patent. The relevant portions of that explanation are repeated below.

Any scission into the human body is detrimental to the human body and invariably results in cell loss. The need to keep cell loss to a minimum is particularly crucial during any surgical procedure performed on delicate and irreplaceable tissues, such as the tissues of the eye, nerves, etc.

The cornea of the eye is comprised of five layers: epithelium, Bowman's membrane, stroma, Descemet's membrane, and endothelium. The endothelium layer is particularly vulnerable to trauma as the endothelial cells are infrequently, if ever, replaced as a normal process in the adult life. The endothelium is principally responsible for the maintenance of the proper state of hydration of the stromal layer. The stromal layer has a tendency to imbibe fluid, a tendency which is counter-balanced by outward fluid transport via the endothelium. If the proper fluid balance is not maintained in the stromal layer, the cornea thickens and the characteristic transparency of the cornea is lost. Accordingly, cell loss or damage in the endothelial layer will result in decreased vision. Failure of the endothelium to perform its fluid transport function for short periods of time will result in corneal thickening and visual clouding. Because of the importance of, and the vulnerability of, the endothelial layer, it is necessary during eye surgery, such as cataract and retinal surgery or corneal transplants, to make provisions for the protection of the endothelial cells.

A significant factor causing cell loss during tissue scission is the traumatic change in environment experienced by the internal cells. Exposure to the atmosphere presents a far different environment for the cells than is provided by the natural fluids in which they are bathed. To simulate the natural cellular environment and thereby prevent cell damage, exposed tissue during surgery is frequently irrigated in solutions which attempt to approximate natural body fluids. The value of bathing eye tissue during surgery to prevent cell damage has long been recognized. For internal ocular tissues, such as the endothelium, the aqueous humor is the natural bathing fluid and, hence, an ophthalmic irrigating solution intended to protect the endothelium should as closely as possible resemble the aqueous humor.

Of primary concern in a tissue irrigating solution is that the osmolality of the solution be generally isotonic with cellular fluids so as to maintain equal osmotic pressure within and without the cell membranes. To this end, one of the early ophthalmic irrigating solutions was isotonic (0.9%) saline. However, as has long been recognized, isotonic saline is quite inadequate as an ophthalmic irrigating solution and has been shown to result in endothelial cell swelling, cell damage, and consequent corneal clouding.

Because of the inadequacy of isotonic saline, various alternative electrolyte solutions have been proposed as ophthalmic irrigating solutions in attempts to provide solutions which more closely resemble the aqueous humor and prevent cell damage and corneal clouding. Standard electrolyte solutions primarily intended for injection solutions, such as Ringer's solution and lactated Ringer's solution, have been used as ophthalmic irrigating solutions because of their wide availability as sterile solutions.

A solution intended for ophthalmic irrigation known as "balanced salt solution" has also been developed. Balanced salt solution contains the essential ions, calcium, sodium, potassium, magnesium and chloride in generally optimal concentrations for ocular tissue, and has an acetate-citrate buffer system which is compatible with divalent calcium and magnesium ions.

The various electrolyte solutions used for ophthalmic irrigation have been improvements over normal saline by providing necessary ions in addition to $Na^+$ and $Cl^-$ as provided by isotonic saline. $Mg^{++}$ is an important cofactor for adenosine triphosphatase, an enzyme which plays an important role in mediating the fluid transport pump in the eye. $Ca^{++}$ is necessary to maintain the endothelial junction. $K^+$ is an important factor in many biochemical processes, and the fluid transport pump of the endothelium requires a proper $Na^+/K^+$ ratio.

During eye surgery and particularly during surgery which requires extended periods of time, proper electrolytic balance alone is insufficient to retain normal corneal thickness. To maintain proper corneal thickness and prevent cell damage, an irrigating solution in addition to electrolytic balance must provide metabolic support and must particularly provide factors needed for the enzyme-mediated $Na^+/K^+$ pump system through which excess fluid is removed from the stroma.

To incorporate factors necessary for sustained metabolism by endothelial cells, glutathione-bicarbonate-Ringers solution ("GBR") was developed in which $NaHCO_3$, glutathione, dextrose and adenosine (an optional ingredient) are added to Ringer's solution. Bicarbonate, dextrose and glutathione have been shown to be important factors in maintaining structural integrity of endothelial cells. Bicarbonate is included because the aqueous humor has a bicarbonate buffer system; dextrose (d-glucose) provides a substrate for various metabolic pathways; and glutathione has been shown to aid the metabolic pump mechanism by maintaining proper $Na^+/K^+$ adenosine-triphosphatase. GBR has been shown effective in maintaining corneal thickness and endothelial cell integrity for up to three hours.

While the effectiveness of a GBR ocular irrigating solution has been known for many years, prior to the early 1980's its use in surgery was quite limited due to stability and sterility problems. It is to be appreciated that sterility of an ophthalmic irrigating solution is absolutely essential. To insure sterility, it is desirable that an irrigating solution be prepackaged so that the quality and sterility may be closely monitored and tested as contrasted with an extemporaneously mixed solution as might be prepared in a hospital pharmacy. The solution will perfuse the eye in essentially a closed system where even a small number of organisms, such as pseudomonas aeruginosa, can produce an overwhelming endophthalmitis.

GBR may not be prepackaged due to the long term incompatibility and/or instability of its various moieties. Of the moieties added to Ringer's solution to formulate GBR, bicarbonate is perhaps the most important. The bicarbonate as well as the phosphate in a bicarbonate-phosphate buffer system may form insoluble precipitates with $Mg^{++}$ and $Ca^{++}$. While at the ionic concentrations useful in ophthalmic irrigation, precipitation is not a problem in freshly prepared solution, long-term storage is proscribed. As insoluble crystals introduced into the eye will cloud vision, the importance of keeping a tissue irrigating solution free of insoluble precipitates may be readily appreciated.

Complicating the maintenance of GBR's stability is the fact that the pH of GBR will gradually increase due to the inadequacy of the bicarbonate-phosphate buffer. To provide proper pit, i.e., about 7.4, the pH of the original GBR solutions prepared in the hospital pharmacy had to be monitored and adjusted with $CO_2$ immediately prior to use and even during use. The chances for contamination during pH adjustment was great.

A further factor which proscribes long-term storage of GBR is the unavailability of a proper pH at which all of the moieties are stable. Several moieties of GBR are unstable at the physiological pH of about 7.4. Below a pH of about 8, bicarbonate generally decomposes to $CO_2$, resulting both in a loss of bicarbonate concentration and increased pH. On the other hand, glucose stability requires a much lower pH. Glutathione, while biologically effective either in reduced or oxidized form, is preferred in the oxidized form because the reduced form quickly oxidizes in aqueous solutions, preventing proper labeling of the irrigating solution. Oxidized glutathione (glutathione disulfide) is unstable over extended periods of time at a pH of above about 5. The concentration of glutathione may also decrease to an unacceptable concentration when stored over long periods of time in admixture with all other components. Because of the demonstrated efficacy of GBR as an ocular irrigating solution, it was highly desirable to provide a formulation which contains the essential factors found in GBR and which could be stored in a sterilized form for use in eye surgery. The invention described in U.S. Pat. No. 4,550,022 provided such a product. An embodiment of the two-part irrigating solution described in U.S. Pat. No. 4,550,022 known as "BSS Plus® Intraocular Irrigating Solution" was introduced by Alcon Laboratories, Inc., Fort Worth, Tex., in the early 1980s.

Ophthalmic irrigating solutions such as BSS Plus® Intraocular Irrigating Solution serve to maintain the physical integrity and function of ophthalmic tissues. The chemical composition of such solutions mimics that of the fluid naturally present within the eye (i.e., "aqueous humor"). Although such solutions are well-suited to maintain the normal function of ophthalmic tissues, these solutions are not directly useful in treating or preventing abnormalities such as acute elevations of intraocular pressure associated with intraocular surgical procedures. Since elevations of intraocular pressure during ophthalmic surgical procedures is a potentially serious problem, there has been a need for an improved ocular irrigating solution which not only maintains the physical integrity and function of ophthalmic tissues, but also controls the intraocular pressure of the patient. The present invention is directed to satisfying this need.

U.S. Pat. No. 5,212,196 (House, et al.) describes the topical use of clonidine derivatives to control IOP in connection with surgical procedures, particularly procedures involving the use of a laser. A product based on the invention described in that patent has been marketed by Alcon Surgical, Inc., Fort Worth, Tex., as IOPIDINE® (apraclonidine hydrochloride) Sterile Ophthalmic Solution. The '196 patent does not disclose the intraocular use of clonidine derivatives for purposes of controlling IOP, nor does it disclose the use of an irrigating solution of the type described herein as a vehicle for intraocular administration of such compounds.

SUMMARY OF THE INVENTION

The present invention is directed to the provision of an improved irrigating solution which is useful in the control of intraocular pressure elevations associated with ophthalmic surgery. More specifically, the invention is directed to irrigating solutions comprising: one or more drugs for controlling intraocular pressure, a free radical scavenger to protect corneal endothelial cells, electrolytes to maintain the stability of ophthalmic tissues, an energy source to satisfy the metabolic requirements of corneal endothelial cells and other ophthalmic tissues during surgical procedures, bicarbonate to maintain the fluid pump system of corneal endothelial cells and other ophthalmic tissues, and a buffer.

Elevations of intraocular pressure can damage the optic nerve head, and thereby impair normal visual function. Such damage can result from minor elevations of intraocular pressure over prolonged periods, or relatively large increases associated with surgical trauma. The present invention is primarily directed to the control of the latter type of intraocular pressure elevations.

The invention has a number of advantages relative to prior methods and compositions for controlling intraocular pressure elevations in connection with ophthalmic surgical procedures. A principal advantage is that the irrigating solutions of the invention perform multiple functions. The solutions prevent cell necrosis and maintain normal cellular functions during ocular surgical procedures, as discussed above, but also control intraocular pressure. The extemporaneous addition of parenteral IOP preparations to ophthalmic irrigating solutions at the time of surgery presents several significant risks, such as the risk of an improper concentration of the IOP drug being utilized. The present invention eliminates these risks by providing an ophthalmic pharmaceutical composition which is adapted for use as an intraocular irrigant. Moreover, the invention enables a very small dose of an IOP controlling agent to be utilized, relative to the dose required if the agent were topically applied to the cul de sac of the eye in accordance with conventional treatment methods. The use of such a small dose is made possible by the direct application of the IOP controlling agent to intraocular tissues, thereby eliminating the need for the agent to traverse the epithelial, endothelial and stromal cell layers. Other advantages of the compositions of the present invention include: (1) delivery of a specified, controlled dose of an IOP controlling agent to the patient, (2) assurance that the composition is sterile at the time of use, (3) elimination of chemical preservatives and other ingredients of parenteral preparations which are potentially damaging to intraocular tissues and (4) adaptation of the pH, osmolality and buffering capacity of the composition so that it is ideally suited for intraocular use.

DESCRIPTION OF PREFERRED EMBODIMENTS

The drugs utilized in the irrigating solutions of the present invention to control intraocular pressure must be at least partially soluble in water. The preferred classes of drugs include beta-blockers, alpha adrenergic agonists, muscarinic agonists, carbonic anhydrase inhibitors, angiostatic steroids and prostaglandins. Beta-blockers and alpha adrenergic agonists are particularly preferred.

The beta-blockers which may be utilized in the present invention include all pharmaceutically acceptable compounds which are capable of reducing the production of aqueous humor when applied topically to the eye. As utilized herein, the term "beta-blocker" means a compound which acts to block beta-1 and/or beta-2 receptors :from stimulation by means of binding with those receptors, and has the ability to control intraocular pressure. Beta blockers may be generally identified by the following structure:

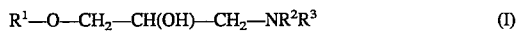

$$R^1\text{—O—CH}_2\text{—CH(OH)—CH}_2\text{—NR}^2R^3 \qquad (I)$$

wherein: $R^1$ is a substituted or unsubstituted cyclic or aliphatic moiety; cyclic moieties include mono- and polycyclic structures which may contain one or more heteroatoms selected from C, N, and O; $R^2$ and $R^3$ are independently selected from H and substituted and unsubstituted alkyl. With regard to beta-blockers of structure (I), above, the following references are incorporated herein by reference:
*Annual Reports in Medicinal Chemistry*, vol. 14, pages 81–87 (1979);
*J. Med. Chem.*, vol. 26, pages 1570–1576 (1983);
ibid., vol. 27, pages 503–509 (1984);
ibid., vol. 26, pages 7–11 ( 1983);
ibid., vol. 26, pages 1561–1569 (1983);
ibid., vol. 26, pages 1109–1112 (1983);
ibid., vol. 26, pages 950–957 (1983);
ibid., vol. 26, pages 649–657 (1983); and
ibid., vol. 26, pages 352–357 (1983).

Specific examples of beta-blockers which may find use in the present invention include acebutolol, adimolol, alprenolol, atenulol, avotinolol, betaxolol, befunolol, bevantolol, bisoprolol, bopindolol, bucomolol, bupranolol, butidrine, bunitolol, bunolol, butocrolol, butoamine, carazolol, carteolol, celiprolol, cetamolol, cicloprolol, diacetolol, draquinolol, epanolol, esmolol, exaprolol, hepunolol, idenolol, iprocrolol, isoxaprolol, labetolol, levobunolol, mepindolol, metipranolol, metoprolol, moprolol, nadolol, nifenalol, oxprenolol, pamatolol, penbutolol, pindolol, practolol, procinolol, pronethalol, propranolol, SKF 95018, sotalol, tazolol, tienoxolol, timolol, tiprenolol, tolamolol, toliprolol, and xamoterol. The most preferred beta-blocker is betaxolol. Other preferred beta-blockers include timolol, levobunolol, carteolol, metipranolol, and pindolol. All of the foregoing compounds are known.

The compositions of the present invention will typically contain one or more of the above-described beta-blockers in an amount of about 0.001 to 0.1 percent by weight, based on the total weight of the composition ("wt. %").

The alpha adrenergic agonists utilized in the present invention include all pharmaceutically acceptable compounds which are capable of controlling intraocular pressure by means of binding with alpha adrenergic receptors, particularly alpha-2 receptors. Such compounds may be more specifically referred to as "alpha-2 agonists".

The alpha-2 agonists which can be employed in the compositions of the present invention include all pharmaceutically acceptable compounds which have alpha-2 agonist activity and are effective in controlling intraocular pressure. Preferred alpha-2 agonists include clonidine, a substituted 2-(arylimino) imidazolidine, and derivatives thereof, including the compounds described in U.S. Pat. Nos. 4,461,904; 4,515,800; and 4,517,199. The entire contents of these three patents are hereby incorporated in the present specification by reference. A preferred group or class of clonidine derivatives are trisubstituted 2-(phenylimino) imidazolidines of formula:

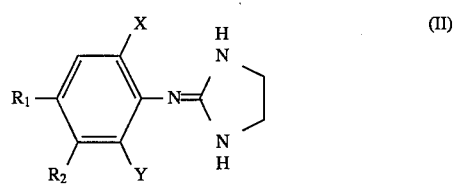

wherein: $R_1$ and $R_2$ are selected from H, OH, NHR' and

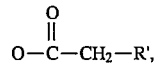

$$O\text{—C—CH}_2\text{—R'},$$

with R' being selected from H and $C_1$–$C_4$ alkyl, provided that one of $R_1$ and $R_2$ is hydrogen; and X and Y are selected from Br, Cl, $CH_3$ and $CH_2CH_3$. Specific examples of compounds from this group are set forth in Table 1 below:

TABLE 1

| Compound | $R_1$ | $R_2$ | X | Y |
|---|---|---|---|---|
| 1 | $NHCH_3$ | H | $CH_3$ | $CH_3$ |
| 2 | $NHCH_3$ | H | $CH_2CH_3$ | $CH_2CH_3$ |
| 3 | $NHCH_3$ | H | Cl | Cl |
| 4 | $NH_2$ | H | Br | Br |

A group of especially preferred clonidine derivatives of formula (II) are those in which $R_1$ and $R_2$ are selected from H and $NH_2$, provided that one of $R_1$ and $R_2$ is H, and X and Y are selected from Cl, $CH_3$, and $CH_2CH_3$. Specific examples of compounds from this group are set forth in Table 2 below:

TABLE 2

| Compound | $R_1$ | $R_2$ | X | Y |
|---|---|---|---|---|
| 5 | H | $NH_2$ | $CH_3$ | $CH_3$ |
| 6 | $NH_2$ | H | $CH_2CH_3$ | $CH_2CH_3$ |
| 7 | H | $NH_2$ | Cl | Cl |
| 8 | $NH_2$ | H | $CH_2CH_3$ | Cl |
| 9 | $NH_2$ | H | $CH_3$ | Cl |
| 10 | $NH_2$ | H | $CH_2CH_3$ | $CH_3$ |
| 11 | $NH_2$ | H | $CH_3$ | $CH_3$ |
| 12 | H | $NH_2$ | $CH_2CH_3$ | $CH_2CH_3$ |
| 13 | $NH_2$ | H | Cl | Cl |

Of these specific examples, p-amino clonidine (i.e., Compound 13) has been found to be particularly well-suited for use in the present invention.

Another preferred group of clonidine derivatives are those wherein $R_1$ and $R_2$ are both H and X and Y are selected from Br, Cl, $CH_3$ and $CH_2CH_3$. Clonidine (X and Y=Cl) is included in this group. Among this group, compounds wherein at least one of X and Y is alkyl are particularly preferred. Compounds of this type are described, for example, in U.S. Pat. No. 3,468,887, and *J. Med. Chem.*, vol. 19, pages 1049–54 (1976); the contents of these publications relating to the structure, preparation and physical properties of clonidine derivatives, particularly substituted 2-(arylimino) imidazolidines, are incorporated herein by reference. Specific examples of compounds from this group are set forth in Table 3 below:

TABLE 3

| Compound | $R_1$ | $R_2$ | X | Y |
|---|---|---|---|---|
| 14 | H | H | $CH_2CH_3$ | $CH_2CH_3$ |
| 15 | H | H | $CH_2CH_3$ | $CH_3$ |
| 16 | H | H | Cl | $CH_2CH_3$ |
| 17 | H | H | Cl | Cl |

In addition to the 2-(arylimino) imidazolidines identified above, other groups or classes of alpha-2 agonists which may be utilized in the present invention include 2-(arylimino) oxazolidines; 2-(arylmethylene) imidazolidines; 2-(arylimino) pyrrolidines; arylalkylaminoguanidines, such as aryl-imidazoquinazolines and phenylacetylguanidines; and 2-(phenylimino) diazocyclopentenes. All of these groups of drugs may be referred to as being clonidine derivatives or "clonidine-like" drugs. A comprehensive discussion of the properties of clonidine and clonidine-like compounds is presented in a publication by Timmermans, et al., titled "Structure-Activity Relationships in Clonidine-Like Imidazolidines and Related Compounds", (pages 1–97, published in 1980 by Gustav Fischer Verlag, of Stuttgart and New York). The entire contents of that publication are hereby incorporated in the present specification by reference. As indicated by Timmermans, et al., the molecular structure of clonidine consists of three parts: an aromatic (i.e., aryl) portion, a bridge, and an imidazolidine moiety. Timmermans, et al., disclose many compounds which have been produced by modifying one or two of these three parts, but which retain one of the three parts intact. For purposes of the present specification, all such compounds are defined as being "clonidine derivatives."

The compositions of the present invention will typically contain one or more of the above-described alpha-2 agonists in an amount of about 0.001 to 0.1 wt. %.

The irrigating solutions of the present invention also include an amount of an antioxidant or free radical scavenger effective to protect the corneal endothelial cells and maintain normal function of those cells. The photochemical generation of active oxygen is a well known chemical phenomenon. The transparency of the cornea, aqueous humor, lens and the retina allows a unique situation for an incessant photochemical generation of oxygen radicals. This phenomenon is generally associated with long exposures to light, such as may be incurred during cataract surgery or other intraocular surgical procedures. Inclusion of an antioxidant/free radical scavenger in an irrigating solution protects the eye against damage which might otherwise be caused by the oxygen free radicals. The preferred antioxidants and free radical scavengers include beta carotene, ascorbic acid, vitamin E, glutathione and cysteine, as well as esters, and analogues and other equivalents of these compounds. The most preferred antioxidant/free radical scavenger is glutathione. The solutions will contain one or more antioxidant/free radical scavengers in a concentration of from about 0.001 to about 0.1 wt. %.

The solutions further comprise: electrolytes in an amount effective to maintain tissue stability; an energy source, such as dextrose, in an amount effective to satisfy the metabolic requirements of corneal endothelial cells and other ophthalmic tissues during the surgical procedure; an amount of bicarbonate effective to maintain the fluid pump system of corneal endothelial cells and other ophthalmic tissues; and a buffer in an amount sufficient to maintain the pH of the composition in the range of 6.8 to 8.0. The present invention may be embodied in various types of ophthalmic irrigating formulations, but will generally be provided in the form of an aqueous solution. As will be appreciated by those skilled in the art, some of the components of the formulations may need to be segregated prior to the time of use, due to considerations involving the chemical stability of certain components, the potential for adverse chemical interactions between certain components, and the methods of sterilization suitable for certain components, as discussed above under the heading "Background of the Invention".

The most preferred embodiment of the present invention is a two-part product similar to BSS Plus® Intraocular Irrigating Solution. The compositions of the two parts are such that each is individually stable and may be separately stored for long periods. When mixed together the two parts form a tissue irrigating solution that may be used for surgery during the next 24 hours. The mixed solution is useful for ocular surgery as it contains the necessary factors to maintain endothelial cell integrity and corneal thickness during ocular surgery. The combined irrigating solution contains the necessary ions for tissue stability, $Ca^{++}$, $Mg^{++}$, $Na^+$, $K^+$ and $Cl^-$ in a bicarbonate-phosphate buffer as well as reduced glutathione and dextrose. The electrolytes are provided in proportions conducive to maintaining the physical integrity and metabolism of corneal endothelial cells and other ocular tissues. For this purpose, the irrigating solution will typically contain from about 50 to about 500 millimoles per liter ("mM/l") $Na^+$, from about 1 to about 10 mM/l $K^+$, from about 0.1 to about 5 mM/l $Ca^{++}$, from about 0.1 to about 10 mM/l $Mg^{++}$ and from about 50 to about 500 mM/l $Cl^-$. To maintain the osmotic stability of the cells, the osmolality is between about 260 and about 330 mOsm and preferably about 290–310 mOsm. So as to closely match the physiological pH of 7.4, the pH of the final irrigating solution is between about 6.8 and about 8.0 and preferably about 7.2–7.8. To maintain the fluid pump system, the bicarbonate concentration in the combined irrigating solution is between about 10 and about 50 mM/l. To stabilize the pH, an additional buffering agent is provided. Preferably the buffering agent is phosphate which is provided in sufficient quantity so that final phosphate concentration of the irrigating solution is between about 0.1 and about 5 mM/l. The final irrigating solution contains between about 1 and about 25 mM/l dextrose and between 0.01 and about 3 mM/l of glutathione.

The basic solution provides the phosphate and bicarbonate buffering moieties, preferably in the form of dibasic sodium phosphate and sodium bicarbonate. The pH of the basic solution is adjusted to about the physiological pH, of 7.4, preferably to between about 7.2 and about 7.8. As hereinbefore mentioned, the pH of a bicarbonate-containing solution is preferably above about 8.0 to prevent decomposition of the bicarbonate. It has been found, however, that the bicarbonate may be stabilized if it is added to a solution with a pH of above about 8 and thereafter adjusted to a pH between 7 and 8. Accordingly, when the basic solution is prepared, $Na_2HPO_4$ is added prior to the addition of $NaHCO_3$, so that $NaHCO_3$ is dissolved in a solution with a pH of between about 8 and 9. The solution is thereafter adjusted with dilute acid, such as $H_2SO_4$, $H_3PO_4$ or HCl, to the desired final pH of the basic solution. Alternatively, carbon dioxide may be added to adjust the pH.

Potassium and additional sodium are provided in the basic solution in the form of sodium and potassium salts, such as sodium or potassium chlorides, sulfates, acetates, citrates, lactates, and gluconates. The sodium and potassium are compatible with all of the moieties present in the finished tissue irrigating solution, and sodium chloride and potassium chloride may be added to either solution or divided between the solutions. However, in view of the fact that the basic solution provides the buffer system, the pH of the final irrigation solution may be added to adjust the pH.

The acidic solution provides the $Ca^{++}$ in the form of calcium chloride, the $Mg^{++}$ in the form of magnesium chloride, the glutathione and the dextrose. The pH is adjusted to below about 5 to provide long-term stability to the dextrose and glutathione.

Because of the requirement that the acidic solution have a low pH, it is preferable that the volume of the basic solution greatly exceed the volume of the acidic solution and that the acidic solution contain no buffering agents. The acidic solution may be adjusted below a pH of about 5 with a relatively small amount of HCl. Because the acidic solution is unbuffered, its pH is a reflection of the acid concentration and less acid is needed to adjust the pH of a small volume. The large volume of buffered basic solution may be adjusted very close to the final pH of the irrigating solution and will be relatively unaffected by the addition of the small volume of the acidic solution. Preferably, the ratio of the basic solution volume to the acidic solution volume is about 10 to 1 to about 40 to 1.

The basic solution and the acidic solution are sterilized and separately bottled or contained under sterile conditions by standard techniques, such as autoclaving, or use of sterilizing filters, but preferably by heat sterilization. Typically, the basic solution, which preferably contains only inorganic moieties, is autoclave& whereas the acidic solution, which preferably contains the organic components, is microfiltered. To avoid the need for measuring volumes in the hospital which may introduce possible error and/or contamination, it is highly preferred that particular volumes of the basic and acidic solutions be bottled so that adding the entire content of a container of the acidic solution to the entire content of a container of the basic solution results in the correctly formulated tissue irrigating solution. The solutions may be mixed up to 24 hours before a surgical procedure without the occurrence of significant pH change and without the formation of detectable precipitates and without degradation.

Precautions to maintain sterility of the solutions and to insure correct mixing of the acidic and basic solutions cannot be overdone. While the manufacturer may take all due precautions to maintain quality control, carelessness by a technician may render all such precautions for naught. Any opening of a container, no matter how carefully performed, increases the likelihood of contamination in the contents. As one method of substantially eliminating the possibility of improper mixing and to reduce the likelihood of contamination, the solutions may be shipped in a container having a first chamber for the basic solution, an isolated second chamber for the acidic solution and means to communicate the chambers without opening the container. The use of such containers are known for the shipment of multi-part medical solutions. As one example, a container may have a lower chamber containing a measured volume of the basic solution separated by a membrane from an upper chamber containing a measured volume of the acidic solution. The container cap may include a plunger means which, when depressed, causes a sharp point of blade depending therefrom to break the membrane. The container is thereafter agitated, as by shaking, to complete the sterile mixing in proper volume of the acidic and basic solutions.

The proper mixing of the acidic and basic solutions may also be carried out by aseptically removing the acidic solution from its package with a sterile syringe and needle and aseptically adding the acidic solution to the contents of the basic solution package through the rubber stopper. Alternately, a sterile double-ended needle can be used to transfer the acidic solution to the basic solution by aseptically inserting one end of the needle into the vial containing the acidic solution and then aseptically inserting the other end of the needle into the basic solution package, whereby the vacuum that is maintained therein transfers the acidic solution to the basic solution and is mixed. The two-part solution of the present invention also provides an advantage as to safety if a technician should fail to properly mix the two solutions. The larger volume basic solution is physiologic so that there is less chance of toxicity if the basic solution were used with the acidic solution being mixed therewith.

The present invention may be embodied in various types of formulations. Representative formulations are described in the following examples.

EXAMPLE 1

The following two-part formulation is similar to the BSS Plus® Intraocular Irrigating Solution available from Alcon Laboratories, Inc., Fort Worth, Tex., USA. That product, which is described in U.S. Pat. No. 4,550,022 (Garabedian, et al.), consists of two solutions referred to as "Part I" and "Part II", respectively. The following description illustrates how that product or similar products could be modified to incorporate the present invention.

Part I (basic solution) is made by dissolving sodium chloride, potassium chloride, and anhydrous dibasic sodium phosphate in water for injection at about 20° C. Then sodium bicarbonate is added and dissolved. Additional water for injection is added to make the desired volume and 1N HCl is added to adjust the pH to about 7.4. The solution is then passed through a 0.45 micron Millipore filter and placed in a bottle. The filled bottle is then stoppered, vacuumed and sealed. The sealed bottle is sterilized by autoclaving at 121° C. for about 23 minutes.

Part II (acidic solution) is made by dissolving calcium chloride dihydrate, magnesium chloride hexahydrate, dextrose, and glutathione in water for injection. The solution is then sterile filtered through a 0.22 micron membrane filter and aseptically filled into a presterilized bottle and sealed with a presterilized rubber stopper.

One or more drugs for controlling intraocular pressure ("IOP Drug(s)") may be added to either the basic solution or the acidic solution, depending on the PKA of the drug(s) selected.

When Parts I and II are combined, the composition of the resulting formulation is as follows:

| Ingredients | Concentration (mM/l) |
| --- | --- |
| Oxidized Glutathione | 0.01–3.0 |
| Para-Amino Clonidine | 10–100 |
| Bicarbonate | 1–50 |
| Calcium | 0.1–5 |
| Magnesium | 0.1–10 |
| Potassium | 1–10 |
| Sodium | 50–500 |
| Phosphate | 0.1–5 |
| Glucose | 1–25 |
| Chloride | 50–500 |
| Sodium Hydroxide and/or | Adjust pH |
| Hydrochloric Acid | Adjust pH |
| Water for Injection | q.s. |

EXAMPLE 2

The following formulation is a more specific example of the Part I solution described in Example 1 above:

| Ingredients | Concentration Grams/Part I (480 ml) | Concentration mg/ml |
| --- | --- | --- |
| Para-Amino Clonidine | 0.48 | 1.0 |
| Sodium Chloride, USP | 3.5712 | 7.440 |
| Potassium Chloride, USP | .1896 | .395 |
| Dibasic Sodium Phosphate | .2078 | .433 |
| Sodium Bicarbonate | .1261 | .263* |
| Purge with $CO_2$ to Adjust pH | | |
| Water for Injection | q.s. 480 ml | |

*Includes 20% excess

The invention may also be embodied in products formulated or configured differently from the two-part product described above. For example, the acidic solution containing glutathione can be lyophilized (i.e., freeze-dried) following preparation and then reconstituted as a solution prior to use. This type of formulation is described in U.S. Pat. No. 4,975,419.

What is claimed is:

1. A pharmaceutical composition for irrigating ophthalmic tissue and controlling intraocular pressure during an intraocular surgical procedure comprising:
    an effective amount of a drug for controlling intraocular pressure selected from the group consisting of beta-blockers, alpha adrenergic agonists, muscarinic agonists, carbonic anhydrase inhibitors, angiostatic steroids, and prostaglandins;
    an amount of an antioxidant/free radical scavenger effective to maintain normal function of corneal endothelial cells selected from the group consisting of beta carotene, ascorbic acid, vitamin E, glutathione, and cysteine;
    electrolytes comprising, $Na^+$, $K^+$, $Ca^{++}$, $Mg^{++}$, $Cl^-$, bicarbonate, and phosphate in an amount effective to maintain tissue stability;
    an energy source in an amount effective to satisfy the metabolic requirements of corneal endothelial cells and other ophthalmic tissues during the surgical procedure;
    said amount of bicarbonate further effective to maintain the fluid pump system of corneal endothelial cells and other ophthalmic tissues; and
    a buffer in an amount sufficient to maintain the pH of the composition in the range of 6.8 to 8.0.

2. A composition according to claim 1, wherein the drug for controlling intraocular pressure is selected from the group consisting of beta-blockers and alpha adrenergic agonists.

3. A composition according to claim 2, wherein the drug for controlling intraocular pressure comprises a beta-blocker.

4. A composition according to claim 3, wherein the beta-blocker is selected from the group consisting of betaxolol, timolol and levobunolol.

5. A composition according to claim 2, wherein the drug for controlling intraocular pressure comprises an alpha adrenergic agonist.

6. A composition according to claim 5, wherein the alpha adrenergic agonist comprises a clonidine derivative.

7. A composition according to claim 6, wherein the clonidine derivative is selected from the group consisting of 2-(arylimino) imidazolidines, 2-(arylimino) oxazolidines, 2-(arylmethylene) imidazolidines; 2-(arylimino) pyrrolidines; arylalkylaminoguanidines; and 2-(phenylimino) diazocyclopentenes.

8. A composition according to claim 7, wherein the clonidine derivative comprises a 2-(arylimino) imidazolidine.

9. A composition according to claim 8, wherein the 2-(arylimino) imidazolidine comprises para-amino clonidine.

10. A composition according to claim 1, wherein the composition comprises a first part and a second part, said first part comprising a basic solution containing the bicarbonate and the buffer, and said second part comprising an acidic solution containing the antioxidant/free radical scavenger, the energy source and the divalent electrolytes, and wherein the drug for controlling intraocular pressure and the monovalent electrolytes are contained in either said first part or said second part.

11. A composition according to claim 1, wherein the antioxidant/free radical scavenger comprises glutathione.

12. A composition according to claim 10, wherein the composition comprises:
    from about 0.001 to about 0.1 wt. % of the antioxidant/free radical scavenger;
    from about 1 to about 25 mM/l of dextrose;
    from about 0.001 to about 4 wt. % of the drug for controlling intraocular pressure;
    from about 50 to about 500 mM/l $Na^+$;
    from about 1 to about 10 mM/l $K^+$;
    from about 0.1 to about 5 mM/l $Ca^{++}$;
    from about 0.1 to about 10 mM/l $mg^{++}$;
    from about 50 to about 500 mM/l $Cl^-$;
    from about 10 to about 50 mM/l bicarbonate; and
    from about 0.1 to about 5 mM/l phosphate.

13. A composition according to claim 12, wherein the drug for controlling intraocular pressure is selected from the group consisting of beta-blockers and alpha adrenergic agonists.

14. A composition according to claim 13, wherein the drug for controlling intraocular pressure comprises a beta-blocker.

15. A composition according to claim 14, wherein the beta-blocker is selected from the group consisting of betaxolol, timolol and levobunolol.

16. A composition according to claim 13, wherein the drug for controlling intraocular pressure comprises an alpha adrenergic agonist.

17. A composition according to claim 16, wherein the alpha adrenergic agonist comprises a clonidine derivative.

18. A composition according to claim 17, wherein the clonidine derivative is selected from the group consisting of 2-(arylimino) imidazolidines, 2-(arylimino) oxazolidines, 2-(arylmethylene) imidazolidines; 2-(arylimino) pyrrolidines; arylalkylaminoguanidines; and 2-(phenylimino) diazocyclopentenes.

19. A composition according to claim 18, wherein the clonidine derivative comprises a 2-(arylimino) imidazolidine.

20. A composition according to claim 19, wherein the 2-(arylimino) imidazolidine comprises para-amino clonidine.

21. An improved method of irrigating ophthalmic tissue and controlling intraocular pressure during intraocular surgical procedures which comprises applying to the affected ocular tissue a composition comprising:

an effective amount of a drug for controlling intraocular pressure selected from the group consisting of beta-blockers, alpha adrenergic agonists, muscarinic agonists, carbonic anhydrase inhibitors, angiostatic steroids, and prostaglandins;

an amount of an antioxidant/free radical scavenger effective to maintain normal function of corneal endothelial cells selected from the group consisting of beta carotene, asorbic acid, vitamin E, glutathione, and cysteine;

electrolytes comprising, $Na^+$, $K^+$, $Ca^{++}$, $Mg^{++}$, $Cl^-$, bicarbonate, and phosphate in an amount effective to maintain tissue stability;

an energy source in an amount effective to satisfy the metabolic requirements of corneal endothelial cells and other ophthalmic tissues during the surgical procedure;

said amount of bicarbonate further effective to maintain the fluid pump system of corneal endothelial cells and other ophthalmic tissues; and a buffer in an amount sufficient to maintain the pH of the composition in the range of 6.8 to 8.0.

22. A method according to claim 21, wherein the drug for controlling intraocular pressure is selected from the group consisting of beta-blockers and alpha adrenergic agonists.

23. A method according to claim 22, wherein the drug for controlling intraocular pressure comprises a beta-blocker.

24. A method according to claim 23, wherein the beta-blocker is selected from the group consisting of betaxolol, timolol and levobunolol.

25. A method according to claim 22, wherein the drug for controlling intraocular pressure comprises an alpha adrenergic agonist.

26. A method according to claim 25, wherein the alpha adrenergic agonist comprises a clonidine derivative.

27. A method according to claim 26, wherein the clonidine derivative is selected from the group consisting of 2-(arylimino) imidazolidines; 2-(arylimino) oxazolidines; 2-(arylmethylene) imidazolidines; 2-(arylimino) pyrrolidines; arylalkylaminoguanidines; and 2-(phenylimino) diazocyclopentenes.

28. A method according to claim 27, wherein the clonidine derivative comprises a 2-(arylimino) imidazolidine.

29. A method according to claim 28, wherein the 2-(arylimino) imidazolidine comprises para-amino clonidine.

30. A method according to claim 21, wherein the composition comprises a first part and a second part, said first part comprising a basic solution containing the bicarbonate and the buffer, and said second part comprising an acidic solution containing the antioxidant/free radical scavenger, the energy source and the divalent electrolytes, and wherein the drug for controlling intraocular pressure and the monovalent electrolytes are contained in either said first part or said second part.

31. A method according to claim 30, wherein the antioxidant/free radical scavenger comprises glutathione.

32. A method according to claim 30, wherein the composition comprises:

from about 0.001 to about 0.1 wt. % of the antioxidant/free radical scavenger;

from about 1 to about 25 mM/l of dextrose;

from about 0.001 to about 4 wt. % of the drug for controlling intraocular pressure;

from about 50 to about 500 mM/l $Na^+$;

from about 1 to about 10 mM/l $K^+$;

from about 0.1 to about 5 mM/l $Ca^{++}$;

from about 50 to about 500 mM/l $Cl^-$;

from about 10 to about 50 mM/l bicarbonate; and from about 0.1 to about 5 mM/l phosphate.

33. A method according to claim 32, wherein the drug for controlling intraocular pressure is selected from the group consisting of beta-blockers and alpha adrenergic agonists.

34. A method according to claim 33, wherein the drug for controlling intraocular pressure comprises a beta-blocker.

35. A method according to claim 34, wherein the beta-blocker is selected from the group consisting of betaxolol, timolol and levobunolol.

36. A method according to claim 33, wherein the drug for controlling intraocular pressure comprises an alpha adrenergic agonist.

37. A method according to claim 36, wherein the alpha adrenergic agonist comprises a clonidine derivative.

38. A method according to claim 37, wherein the clonidine derivative is selected from the group consisting of 2-(arylimino) imidazolidines; 2-(arylimino) oxazolidines; 2-(arylmethylene) imidazolidines; 2-(arylimino) pyrrolidines; arylalkylaminoguanidines; and 2-(phenylimino) diazocyclopentenes.

39. A method according to claim 38, wherein the clonidine derivative comprises a 2-(arylimino) imidazolidine.

40. A method according to claim 39, wherein the 2-(arylimino) imidazolidine comprises para-amino clonidine.

* * * * *